(12) United States Patent
Lewellin

(10) Patent No.: US 6,796,893 B2
(45) Date of Patent: Sep. 28, 2004

(54) APPARATUS AND METHOD FOR PROCESSING WORMS

(76) Inventor: Richard Laurance Lewellin, 4 Gerards Way, Tyabb, Victoria 3913 (AU)

( * ) Notice: Subject to any disclaimer, the term of this patent is extended or adjusted under 35 U.S.C. 154(b) by 0 days.

(21) Appl. No.: 10/302,519

(22) Filed: Nov. 22, 2002

(65) Prior Publication Data

US 2004/0102146 A1 May 27, 2004

(51) Int. Cl.$^7$ ................................................ A22B 5/20
(52) U.S. Cl. ...................................... 452/160; 452/198
(58) Field of Search ................................ 452/160, 198, 452/53

(56) References Cited

FOREIGN PATENT DOCUMENTS

| AU | A-59352/86 | 6/1986 |
|---|---|---|
| FR | 2587993 A1 * | 9/1987 |
| WO | WO 91/07480 | 11/1990 |
| WO | WO 97/19600 | 5/1996 |

OTHER PUBLICATIONS

Derwent Abstract 93–011135/02; 14.09.90; Bioker Kisszo-evetkezet; "High protein prepn. of worm (paste)—obtd. by placing worm on gauze, heating, passing through gauze, washing,m centrifuging and grinding to homogeneous pulp and drying".

Derwent Abstract 91–255181/35; 29.12.89; E. Pest; "Prepn. of protein powder—from suspensions of annelids, by centrifuging and drying pref. by lyophilisation".

* cited by examiner

Primary Examiner—Peter M. Poon
Assistant Examiner—David Parsley
(74) Attorney, Agent, or Firm—Rolf Fasth; Fasth Law Offices

(57) ABSTRACT

The apparatus and method for processing worms uses spaced top and bottom surfaces of a rotor set a sufficient distance apart so that worm bodies to be processed touch both surfaces. A splitter is located mid-way between the surfaces and the worm bodies are forced by centrifugal force and by a flow of water in which the bodies are entrained to encounter and to be split by the splitter blade. The top and bottom surfaces are set a sufficient distance apart so that the worm bodies are partially flattened when passing therebetween. The splitter is located so as to be operative to split the central digestive tract of the worm body. An inlet is located in the top surface through which the worm bodies are introduced into the space between the top and bottom surfaces.

18 Claims, 3 Drawing Sheets

APPARATUS AND METHOD FOR PROCESSING WORMS

FIELD OF THE INVENTION

The present invention relates to an apparatus and method for processing worms for providing the processed worm bodies as an end product or for enabling recovery of valuable by-products from the worm bodies.

Valuable by-products can be simple and as 'obvious' as using the worms as a source of protein e.g. to provide a food supplement for feeding to, inter alia, fish in intensive fish farming operations or as a source of omega oils which may be found in economically viable quantities in the bodies of earthworms. For example, the omega-3 fatty acids DHA (docosahexaenoic acid), EPA (eicosopentaenoic acid), and DPA can be found in earthworm bodies and the market price of such fatty acids compounds at 99% purity is over US$50,000 per kilogram. The term 'worm' when used in this specification includes an earthworm or marine worm (Chaetipoda), flat-worm (Platyhelminthes), a round-worm (Nematoda), and other suitable invertebrates.

Before the bodies of worms could be used as a protein source, it would be desirable to cleanse the worm bodies of ingested matter and/or remove the digestive tract and/or remove blood from the worm bodies. Also cleansing the digestive tract would be desirable if the worm bodies are to be processed for recovery of substances therefrom e.g. essential oils, acids, etc. Emptying the digestive tract has been proposed in the past by 'starving' the earthworms e.g. for 24–48 hours by keeping them in moist paper so that they naturally pass ingested matter through their digestive tracts. However, this does not remove the digestive tract or blood from the worm bodies.

It has further been proposed to cut worms longitudinally to expose the insides of the digestive tracts and then washing the split worm bodies. This process and concept has been clearly described in the PCT Patent specification PCT/AU96/00324 (Publication No. WO97/19600) by the present applicant.

In PCT/UA96/000324, the method of processing worms for providing or recovering valuable products from the worm bodies has been claimed and such method includes the steps of exposing the insides of the digestive tracts of the worms along substantially the entire lengths thereof and cleansing the worm bodies to remove ingested matter and/or the exposed digestive tracts.

In one embodiment of PCT Application No. PCT/AU96/00324, the step of exposing the inside of the digestive tracts comprises eversion of the bodies. The eversion of the worm bodies may comprise drawing each worm body onto a pin located concentrically within a passage through which the worm body is fed longitudinally so that the pin partially enters the digestive tract but resistance to continued relative penetration of the pin into the digestive tract preferentially causes the worm body to evert so that the digestive tract is exposed on the outside of the worm body. The worm body may be split lengthwise after eversion so as to enable removal of the worm body from a processing zone where eversion has taken place.

In an alternative embodiment of said PCT application, the step of exposing the inside of the digestive tracts comprises splitting each worm body lengthwise so as to open the digestive tract of the worm lengthwise.

However, the applicant's own prior art as described above may suffer certain disadvantages as follows:

(a) The prior schemes for splitting the worm bodies may be too slow in practice since the time taken to separate, align, and feed worms sequentially may make the throughput rate uneconomical. This may also make the previously proposed apparatus difficult and costly to implement to achieve viable production quantities.

(b) Worm bodies can vary substantially in diameter and length. In the prior art apparatus, there is little tolerance to processing of worms of different diameters. Therefore, there is a need for modified apparatus for processing different sizes of worms. Since lengths of worms can commonly be up to about 15 cm, the prior apparatus has greater difficulty in handling and: aligning such long worm bodies for splitting.

Therefore, there is a need for a simpler, more effective, and more economically viable apparatus and process for splitting the worm bodies.

OBJECTS OF THE INVENTION

It is therefore an object of the present invention to overcome or alleviate at least some of the drawbacks as stated above and to provide an apparatus for effectively processing worms.

It is also an object of the present invention to provide a more effective and preferably economically viable method for processing worms.

SUMMARY OF THE INVENTION

Accordingly, the present invention provides an apparatus for processing worms, the apparatus including:

spaced top and bottom surfaces set a sufficient distance apart so that worm bodies to be processed touch both surfaces when passing therebetween;

at least one splitter located between the surfaces and extending generally parallel to the surfaces to encounter worm bodies that travel between the surfaces, thereby splitting the worm bodies and;

means for applying force to the worm bodies to urge them between the two surfaces and onto the splitter so as to split the worm bodies lengthwise into segments.

In the present specification including in the claims, in interpreting references to "top and bottom surfaces", and later in this specification to "top plate" and "bottom plate" which provide respectively the "top and bottom surfaces", it is to be understood that the use of "top" and "bottom" in referring to the surfaces does not necessarily mean that the two surfaces are horizontal with the top one overlying the bottom one. Although this may be the preferred configuration, in practice the top and bottom surfaces can be inclined to the horizontal and indeed may even be both vertical. Also the surfaces need not necessarily be planar. For example, the surfaces could be generally conical or frusto conical and could be nested together with the required spacing between the surfaces.

In a preferred embodiment, the apparatus applies a centrifugal force to the worm bodies. For this purpose a rotor having spaced top and bottom plates provides respectively the top and bottom surfaces facing each other and spaced apart by the required distance. The rotor in use is arranged to be rotated about an axis passing through the top and bottom plates, preferably substantially through the centres thereof and the worm bodies when passing between the plates move outwardly from the axis of rotation under the radially acting centrifugal forces created by rotation of the rotor.

The means for applying force to the worm bodies includes means for creating a flow of fluid, preferably water, which applies force to the worm bodies to urge them between the two surfaces and onto the splitter.

The splitter may be a single splitter located substantially midway between the surfaces so as to split the worm bodies into two halves along a plane extending through the centres of the worm bodies when they are touching, and preferably partially flattened between, the top and bottom surfaces. The splitter may comprise a splitter blade although a splitter wire may also be possible. The splitter is preferably located so as to be operative to split the central digestive tracts of the worm bodies.

The apparatus preferably includes an inlet or a number of inlets located in the top surface through which the worm bodies are introduced into the space between the top and bottom surfaces. In the case of the apparatus including a rotor with spaced top and bottom plates, the inlet is preferably located substantially centrally at the centre of the top plate through which the axis of rotation of the rotor passes.

The inlet preferably has a flared inlet mouth leading into the space between the top and bottom plates into which worm bodies are introduced so that worm bodies of various diameters are compressed as they pass into the inlet mouth and into the space between the top and bottom surfaces to adopt a common thickness equal to the spacing of the top and bottom surfaces.

The apparatus may include adjustable spacing means enabling the spacing between the top and bottom surfaces to be selectively adjusted for processing differing diameters of worm bodies. The adjustable spacer means may include an arrangement for maintaining the splitter located substantially centrally between the top and bottom surfaces.

The apparatus preferably further includes a collecting zone located adjacent the top and bottom surfaces and into which the worm bodies pass after having been split lengthwise into segments thereby enabling collection of the segments for subsequent processing. In the preferred embodiment the collecting zone surrounds the periphery of the rotor to receive the worm bodies discharged under the centrifugal force.

There is also provided in a second aspect of the invention a method of processing worms including the steps of:

providing an apparatus which includes spaced top and bottom surfaces set a sufficient distance apart so that worm bodies to be processed touch both surfaces when passing therebetween and at least one splitter located between the surfaces and extending generally parallel to the surfaces to encounter worm bodies that travel between the surfaces;

introducing the worm bodies into the apace between the surfaces together with a sufficient flow of fluid; and moving the worm bodies in the flow of fluid between the two surfaces and onto the splitter so as to split the worm bodies lengthwise into segments.

Preferably the step of moving the worm bodies includes applying a centrifugal force to the worm bodies.

In the preferred method for processing worms, the method includes the step of passing the worm bodies through a rotor providing spaced plates which define the top and bottom surfaces, the plates being set at a sufficient distance apart so that worm bodies touch both plates and are preferably partially flattened when passing therebetween, the splitter being located between and extending generally parallel to the plates. Preferably the rotor is rotated at sufficient speed to create centrifugal force acting on the worm bodies and on the water to promote movement of the worm bodies outwardly between the plates to encounter and to be split by the splitter. Preferably the rotational speed is also sufficient to cause the split worm bodies to be thrown outwardly from the periphery of the rotor and to impact against a wall of a collecting zone. Preferably, the impact of the split worm bodies onto the wall of the collecting zone is sufficient to force blood out of the blood vessels of the worm bodies.

The apparatus of the preferred embodiment of the present invention has a number of features working in combination:

i) spaced surfaces of the rotor plates between which worm bodies are introduced so that the worm bodies are at least slightly flattened between the two surfaces;

ii) a splitter located approximately mid-way between the two surfaces and being generally parallel to the surfaces in the region of the splitter; and iii) means for applying force to the worm bodies to urge them between the two surfaces and onto the splitter so as to split the worm bodies lengthwise into segments.

In the preferred method, the worm bodies are introduced in the apparatus of the present invention with a sufficient flow of water which acts as a lubricant and to impart force on the worm bodies to move between the surfaces so that the worm bodies can slide outwardly between the two plates even though they are compressed between the plates at the same time. Without the introduction of the water in significant quantities, the worm bodies may tend to become stuck or jammed in the space between the plates and block further worm bodies travelling outwardly. However, if the rotational speed of the rotor is sufficiently greater, lesser quantities of water could be used. In a preferred embodiment, the centrifugal force created by the rotating rotor throws the water and split worm bodies radially outward from the periphery of the rotor and preferably onto the walls of a collecting zone, the impact of the split worm bodies onto the walls forcing blood out of blood vessels of the worm bodies.

Further cleansing of the split worm bodies may include washing the worm bodies by immersing and agitating the worm bodies in a washing medium so as to loosen remaining ingested matter enabling separation thereof from the bodies.

BRIEF SUMMARY OF THE DRAWINGS

Possible and preferred features of the present invention are shown and illustrated in the accompanying drawings. However, the features illustrated in and described with reference to the drawings are not to be construed as limiting on the scope of the present invention. In the drawings.

DESCRIPTION OF THE PREFERRED EMBODIMENTS

Figure 1:
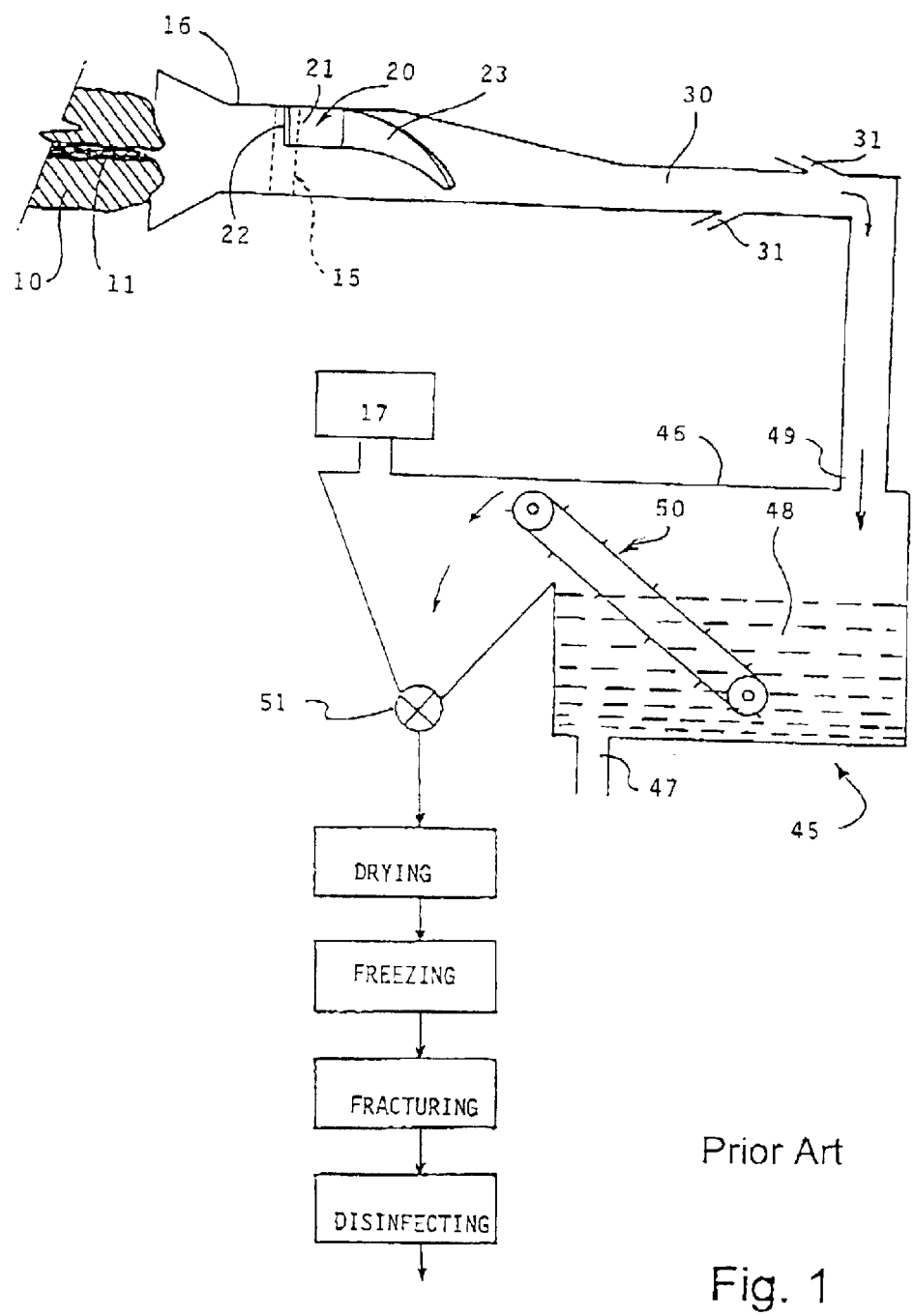
FIG. 1 is a schematic view of a prior art apparatus for processing worm bodies.

In the method involving use of the prior art apparatus of FIG. 1, the method includes the step of exposing the insides of the digestive tracts 11 of worm bodies 10. In the embodiments of FIG. 1 each worm 10 may be slit longitudinally either substantially to the centre of the worm body along which the digestive tract 11 of the worm extends or completely through the body generally diametrically so as to open the gut 11 along the entire length thereof.

In FIG. 1, cutting of the worm longitudinally is achieved by passing the worm body 10 through an aperture 15 or along a passage having a slitting member 20 projecting into the aperture or passage, the slitting member slitting the worm body longitudinally as it passes thereby. The aperture 15 may be comprised by a portion of a tube 16 through which the worm is passed. Preferably the worm body 10 is a close fit within the tube 16 and preferably the worm is drawn through the tube having the slitting member 20 projecting into the tube, the slitting member 20 extending generally radially into the tube, either by a distance substantially equal to half the diameter of the tube 16 or across the entire diameter of the tube. Preferably the diameter of the tube is slightly less than the expected relaxed diameter of the worm to be processed so that the worm body is a close fit within the tube. The worm body 10 is drawn through the tube 16 by applying a vacuum 17 to the tube 16 downstream of the slitting member 20, the worm being introduced into the tube upstream of the slitting member and being drawn into the tube, by the applied vacuum. Because of the restricted diameter of the tube 16, the worm body 10 is closely confined within the tube, thereby allowing a vacuum applied to the tube to draw the worm body through the tube.

Figure 2:
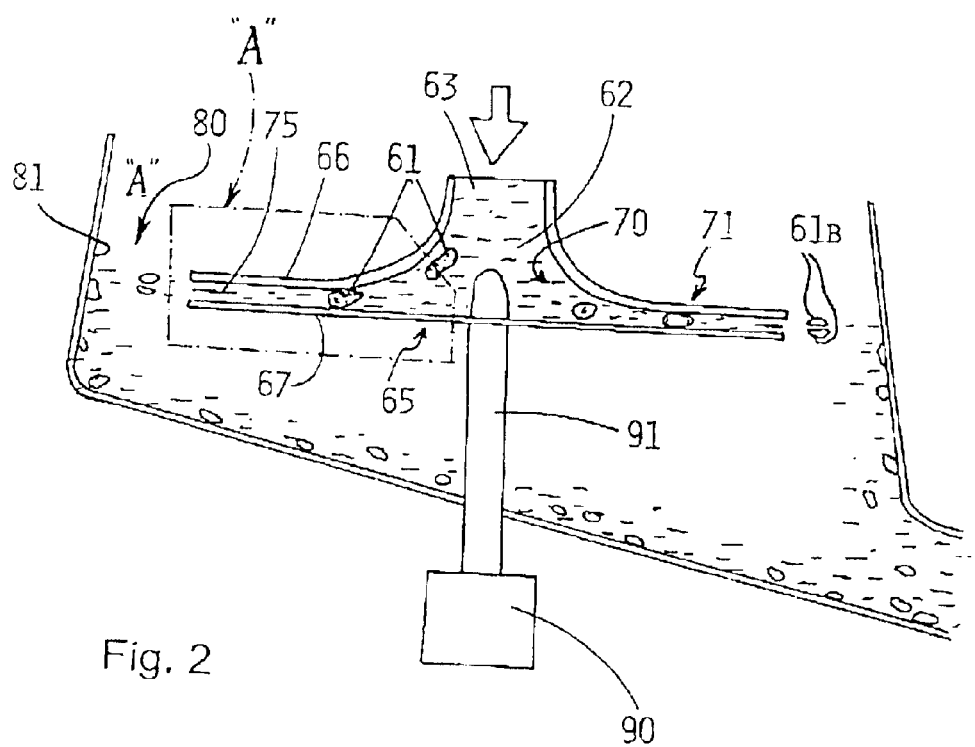
FIG. 2 is a schematic view of an apparatus for processing worms according to the present invention.
Figure 2A:
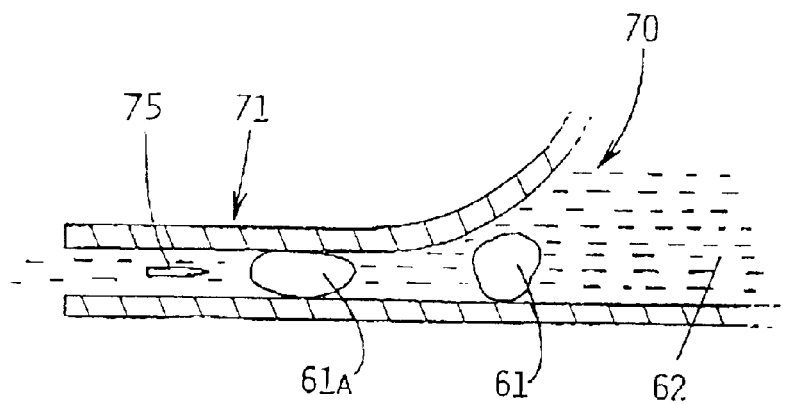
FIG. 2a is an enlarged view of area "A" in FIG. 1.

In FIGS. 2 and 2a, showing an apparatus according to the present invention and illustrating the method, the worm bodies 61 are introduced with a flow of water 62, through a central inlet 63 in top plate 66 and into the space between the top plate 66 and bottom plate 67 of the rotor 65 so that there is little or no air introduced. The water 62 and worm bodies 61 can be regarded as a 'slurry' although the volume of water greatly exceeds the volume of worm bodies. The volume of water 62 between the plates 66, 67 and in the inlet area 63 of the apparatus can be any suitable amount, and depends for example on the diameter and spacing of the plates 66, 67.

The worm bodies 61 and water 62 enter the flared lead-in or mouth 70 in the top plate 66 by action of the flow and assisted by the centrifugal force created by rotation of the rotor. The worm bodies then enter parallel plates section 71 of the rotor 65 which slightly flattens them as shown at 61a in FIG. 2a. Because there is sufficient force generated by the flow and by the rotating rotor 65, the flattened worm bodies 61a then pass the splitter 75 which splits each passing worm body longitudinally through the central digestive tract or gut into respective halves 61b. The splitter 75 is located between the surface planes of the plates 66, 67 which includes the possibilities of being within the peripheries of the rotor 65 as shown at 75, or being located at or just beyond the peripheral exit point as shown at 75a. The splitter 75 can be a splitter blade as illustrated, or can be a wire, water jet, air knife, laser beam, etc.

Each split worm body 61b with its digestive tract or gut split open is thrown by the flow and by centrifugal force outwardly from the rotor 65 and encounters the walls 81 of the surrounding collecting zone 80. The walls 81 are tapered outwardly in a downwards direction so that the split worm bodies and water striking the walls are directed downwardly through the collection zone 80. The striking of the split worm bodies 61b and split gut against the walls 81 shakes loose and separates ingested matter within the gut. The impact of the worm bodies against the walls also forces blood out of the blood vessels in the worm bodies so that the ingested matter and blood are mixed in a slurry within the water. Below the collection zone 80, there can be a screening arrangement (not shown) which collects the split worm bodies 61b and allows the slurry of water with ingesta and blood entrained to pass through the screen.

Figure 3:
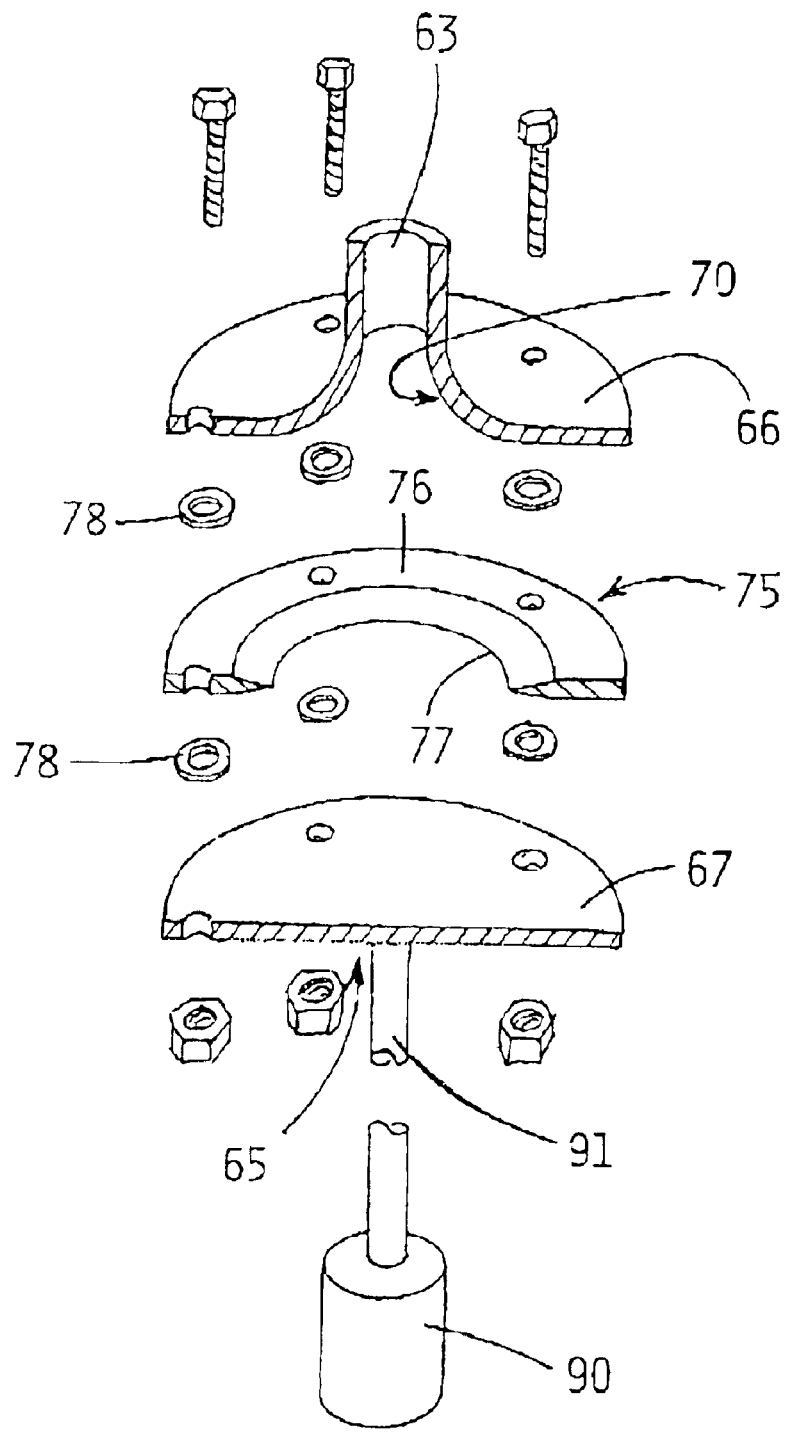
FIG. 3 is a perspective exploded view of the rotor for use in apparatus according to the present invention.

In FIG. 3, the rotor 65 comprises metal plates 66, 67 preferably having diameters determined by the rotational speed and the throughput rate required. As one example only, the diameter may be about 40 cm. The plates 66, 67 can be mounted together as shown in FIG. 3 with the splitter 75 formed by an annular splitter ring 76 having a sharp edge 77 facing radially inwardly and spaced mid-way between the plates. The bottom plate 67 is mounted directly on the shaft 91 of an electric motor 90 (i.e. no gearing) which rotates the assembly e.g. at about 1450 rpm. For longer worms, e.g. about 15 cm in length, larger diameter plates 66, 67 may be desirable, e.g. about 60 cm.

The spacing between the two plates may be for example about 2.9 mm, made up of two spacer washers 78 of 1 mm thickness each, and the annular splitter ring 76 has thickness of 0.9 mm. Worm diameters commonly encountered range from about 2 mm up to 6–7 mm. The spacing 2.9 mm is suitable for worms of about 4 mm diameter. For worms of other diameters, the spacing can be adjusted accordingly e.g. by using different thicknesses of washers 78. Broadly, the spacing of the plates 66, 67 should be slightly less than the diameter of the worms so that the worm bodies are slightly compressed as they pass between the plates. This ensures the central gut through the worm body is centered between the plates and is therefore sliced by the splitter blade. For smaller diameter worms, the spacing would be correspondingly reduced.

The splitter 75 does not need to be mounted so as to rotate with the rotor, but can be mounted externally in the position shown at 75a or projecting slightly into the space between the plates 66, 67, e.g. by being mounted to a frame or to the walls of the collecting zone 80.

Also the plates 66, 67 need not be mounted together with spacers 78 therebetween but can be mounted externally so that there is no obstruction for the worm bodies within the space between the plates. For example, the lower plate 66 can be mounted for rotation on the drive shaft 91 and the upper plate 67 mounted by bearing 93 for rotation coaxial with the shaft 91. Drive to the upper plate 67 can be by any suitable means or possibly may not be needed if there is sufficient rotation imparted by the lower plate to the flow of the worm bodies entrained in the water. External mounting of the plates 66, 67 also enables ready adjustment of the spacing for different diameters of worms by vertical adjustment of the position of one of the plates 66, 67. Elimination of the spacers 78 also makes cleaning of the plates after use easier.

In a further possible variation of the invention described herein, the water may be replaced by or mixed with another fluid such as another solvent, oil, pressurised air, steam or a mixture of such fluids, depending on physical and chemical properties or process effects required.

As an alternative to applying to the worm bodies a centrifugal force by means of a rotor which provides the top and bottom surfaces, a vortex may be created in the fluid flow with the worms entrained in the flow and the top and bottom surfaces may be stationary.

In a preferred embodiment of the present invention, further treatment of the split worm bodies can be conventional, such as drying and pulverising to make protein meal for various purposes.

For extracting valuable components such as oils, esters, acids from the split worm bodies, a distillation process can be used, since these valuable materials are generally volatile compounds that can be evaporated by heating the split worm bodies and distilling the vapours. It is found that essential oils and acids contained within the worm bodies boil or evaporate at a lower temperature than water within the worm bodies so that controlled distillation and fractionating is possible to extract and separate such substances.

Tests carried out on earthworm materials processed according to the present invention have shown significant quantities of omega-3 fatty acids.

In test 1, the upper floating surface scum of a slurry collected beneath the collection zone 80 of the type shown in and described in relation to FIG. 3 was processed to separate the upper solid sediment phase which was dried and subject to gas chromatographic analysis. Results obtained were:

DHA 13.8 mg/100 g
EPA <2 mg/100 g
DPA <2 mg/100 g

In test 2, a dried powder sample of worm bodies processed according to the present invention was analysed and results were:

DHA 113.6 mg/100 g
EPA 882.7 mg/100 g
DPA <5 mg/100 g

The drying may be carried out by solar drying or by artificially heating the worm bodies to eliminate moisture content after which the worm bodies can be frozen and pulverised to produce the particulate substance.

The worm bodies with or without preliminary drying may be frozen by using conventional refrigeration equipment, such as ammonia refrigeration plant, or by cryogenic process. For example, the worm bodies may be frozen by immersing, spraying or exposing the bodies to gas from boiling liquid nitrogen. Preferably, the worm bodies are frozen to a temperature so that they become brittle.

The frozen bodies may be pulverised e.g. in a hammer mill to which the bodies are fed immediately after freezing. The hammer mill components that contact the products may be stainless steel for hygienic purposes. The particulate substance produced may comprise a fine granular free flowing substance suitable for use as a food supplement or animal food or for blending with other food substances, or for processing to manufacture or recover valuable products therefrom. Further drying after pulverising may be desirable.

If the particulate substance is intended for use as a food or food supplement, it is preferably treated prior to storage or use so as to generally sterilise or disinfect at least partially the substance prior to packaging, storage or use. The particulate substance for example may be passed in the form of substantially separate particles through a sterilising radiation flux, e.g. an ultra violet radiation flux. The particulate substance may be pulverised to a fine powder consistency and entrained in air so as to create an aerated suspension of the particulate food substance. The suspension may be passed through a zone in which the particles are exposed to a sterilising radiation flux, or the suspension may be passed to a deaerating means such as a cyclone deaerator, the deaerating means having an outlet at the bottom arranged so that the particles fall gently through the output, the falling particles then falling into an irradiation zone. The process and apparatus of sterilising or disinfecting the particulate substance may be generally as described in Australian Patent Specification No. 59352/86 and reference may be made to the description of the process and apparatus in that specification for such details. The disinfected substance will be expected to have a greater storage life due to the disinfecting process.

Without limiting the scope of the present invention, the method and apparatus of processing worms according to the present invention commence with worms grown in any suitable growing medium on an intensive scale. When the worms have reached an optimum size, they can be readily separated from the growing medium, e.g. by sieving, and then they can be fed to the processing apparatus.

The growing, harvesting and processing of worms can be an intensive operation which can be carried out with little human intervention or direct control and thus minimising associated labour costs.

What I claim is:

1. An apparatus for processing worms, the apparatus comprising:
   spaced top and bottom surfaces set a sufficient distance apart no that worm bodies to be processed touch both surfaces when passing therebetween;
   at least one splitter located between the surfaces and extending generally parallel to the surfaces to encounter worm bodies that travel between the surfaces, thereby splitting the worm bodies; and
   means for applying a centrifugal force to the worm bodies to urge them in an outward direction and between the two surfaces and onto the splitter so as to split the worm bodies lengthwise into segments.

2. An apparatus au claimed in claim 1 wherein the apparatus includes a rotor having spaced top and bottom plates providing respectively the top and bottom surfaces and wherein the means for applying force includes means for rotating the rotor about an axis passing through the top and bottom plates so that the worm bodies located between the surfaces experience the centrifugal force.

3. An apparatus as claimed in claim 2 wherein the means for applying force to the worm bodies further includes mean for creating a flow of fluid which apples force to the worm bodies to urge them between the two surfaces and onto the splitter.

4. An apparatus as claimed in claim 1 wherein the means for applying force to the worm bodies includes means for creating a flow of fluid which applies force to the worm bodies to urge them between the two surfaces and onto the splitter.

5. An apparatus as claimed in claim 1 wherein the spaced top and bottom surfaces are set a sufficient distance apart so that the worm bodies are partially flattened when passing therebetween.

6. An apparatus an claimed in claim 1 and further including adjustable spacing means to enable the spacing between the top and bottom surfaces to be selectively adjusted for processing differing diameters of worm bodies.

7. An apparatus an claimed in claim 1 wherein the splitter is located so as to be operative to split the central digestive tract of the worm body.

8. An apparatus as Claimed in claim 1 wherein the splitter comprises a single splitter located substantially midway between the top and bottom surfaces so as to split the worm bodies into two halves along a plane extending through the centres of the worm bodies.

9. An apparatus an claimed in claim 1 Wherein the splitter comprises a splitter blade having a sharp splitting edge facing in a direction from which the worm bodies approach and encounter the splitter blade.

10. An apparatus an claimed in claim 9 and further including inlet means located in the top surface through which the worm bodies are introduced into the space between the top and bottom surfaces.

11. An apparatus as claimed in claim 2, and further including an inlet located in the top plate through which the worm bodies are introduced into the space between the top and bottom plates, the inlet being located substantially at the centre of the top plate through which the axis of rotation of the rotor passed.

12. An apparatus as claimed in claim 11 wherein the inlet has a flared inlet mouth leading into the space between the top and bottom plates into which worm bodies are introduced so that worm bodies of various diameters are compressed as they pass into the inlet mouth and into the space between the top and bottom surfaces to adopt a common thickness equal to the spacing of the top and bottom surfaces.

13. An apparatus as claimed in claim 1 and further including a collecting zone located adjacent the top and bottom surfaces and into which the worm bodies pass after having been split lengthwise into segments thereby enabling collection of the segments for subsequent processing.

14. An apparatus as claimed in claim 2, and further including a collecting zone surrounding the periphery of the rotor and into which the worm bodies pass after having been split lengthwise into segments and discharged under action of centrifugal force from the periphery of the rotor, thereby enabling collection of the segments for subsequent processing.

15. A method of processing worms comprising the steps of:

providing an apparatus which includes spaced top and bottom surfaces met a sufficient distance apart so that worm bodies to be processed touch both surfaces when passing therebetween and at least one splitter located between the surfaces and extending generally parallel to the surfaces to encounter worm bodies as they travel between the surfaces;

introducing the worm bodies into the space between the surfaces together with a flow of fluid; and applying a centrifugal force to the worm bodies to outwardly move the worm bodies and the flow of fluid between the two surfaces and onto the splitter so as to split the worm bodies lengthwise into segments.

16. A method as claimed in claim 15 wherein the method includes the step of passing the worm bodies through a rotor which has spaced plates which define the top and bottom surfaces, the plates being set at a sufficient distance apart so that the worm bodies touch both the plates, the splitter being located between and extending generally parallel to the plates, the method further including the step or rotating the rotor at sufficient speed to create the centrifugal force acting on the worm bodies to promote movement of the worm bodies outwardly between the plates to encounter and to be split by the splitter.

17. A method as claimed in claim 16 wherein the rotational speed of the rotor is sufficient to cause the split worm bodies to be thrown outwardly from the periphery of the rotor and to impact against a wall of a collecting zone.

18. A method as claimed in claim 17 wherein the impact of the split worm bodies onto the well of the collecting zone is sufficient to force blood out of blood vessels of the worm bodies.

* * * * *